(12) United States Patent
Sertchook et al.

(10) Patent No.: US 9,687,465 B2
(45) Date of Patent: *Jun. 27, 2017

(54) COMPOSITIONS FOR THE TREATMENT OF ROSACEA

(71) Applicant: SOL-GEL TECHNOLOGIES LTD., Ness Ziona (IL)

(72) Inventors: Hanan Sertchook, Gedera (IL); Ofer Toledano, Kfar-Saba (IL); Haim Bar-Simantov, Modi'in (IL)

(73) Assignee: SOL-GEL TECHNOLOGIES LTD., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/686,533

(22) Filed: Nov. 27, 2012

(65) Prior Publication Data

US 2014/0147396 A1  May 29, 2014

(51) Int. Cl.
| | |
|---|---|
| A61K 31/327 | (2006.01) |
| A61K 9/00 | (2006.01) |
| A61K 47/10 | (2017.01) |
| A61K 47/14 | (2017.01) |
| A61K 9/107 | (2006.01) |
| A61K 9/50 | (2006.01) |

(52) U.S. Cl.
CPC .......... *A61K 31/327* (2013.01); *A61K 9/0014* (2013.01); *A61K 9/1075* (2013.01); *A61K 9/501* (2013.01); *A61K 47/10* (2013.01); *A61K 47/14* (2013.01)

(58) Field of Classification Search
CPC .... A61K 31/327; A61K 9/0014; A61K 9/501; A61K 47/14; A61K 9/1075; A61K 47/10
USPC ................. 514/714, 859, 864, 947
See application file for complete search history.

(56) References Cited

U.S. PATENT DOCUMENTS

| | | |
|---|---|---|
| 1,387,107 A | 8/1921 | Carr |
| 1,671,956 A | 5/1928 | McGregor et al. |
| 2,885,366 A | 5/1959 | Iler |
| 3,785,798 A | 1/1974 | Horai et al. |
| 3,826,670 A | 7/1974 | Rees |
| 3,957,971 A | 5/1976 | Oleniacz |
| 4,129,645 A | 12/1978 | Barnett |
| 4,169,069 A | 9/1979 | Unger et al. |
| 4,349,456 A | 9/1982 | Sowman |
| 4,350,681 A | 9/1982 | Fulton |
| 4,361,584 A | 11/1982 | Fulton |
| 4,387,107 A | 6/1983 | Klein et al. |
| 4,444,746 A | 4/1984 | Harvey et al. |
| 4,464,317 A | 8/1984 | Thies et al. |
| 4,497,794 A | 2/1985 | Klein et al. |
| 4,606,913 A | 8/1986 | Aronson et al. |
| 4,671,956 A | 6/1987 | Bouillon et al. |
| 4,686,211 A | 8/1987 | Hara et al. |
| 4,690,825 A | 9/1987 | Won |
| 4,692,329 A | 9/1987 | Klein et al. |
| 4,769,080 A | 9/1988 | Clark et al. |
| 4,891,211 A | 1/1990 | Winston |
| 4,931,362 A | 6/1990 | Zsifkovits et al. |
| 4,960,772 A | 10/1990 | Sebag et al. |
| 4,988,744 A | 1/1991 | Yamamoto |
| 5,086,075 A * | 2/1992 | De Villez ..................... 514/714 |
| 5,126,915 A | 6/1992 | Pepin et al. |
| 5,145,675 A | 9/1992 | Won et al. |
| 5,165,914 A | 11/1992 | Vlock |
| 5,200,334 A | 4/1993 | Dunn et al. |
| 5,223,250 A | 6/1993 | Mitchell et al. |
| 5,269,840 A | 12/1993 | Morris et al. |
| 5,292,801 A | 3/1994 | Avnir et al. |
| 5,387,622 A | 2/1995 | Yamamoto |
| 5,446,028 A | 8/1995 | Klein et al. |
| 5,455,048 A | 10/1995 | Lahmani et al. |
| 5,466,446 A | 11/1995 | Stiefel et al. |
| 5,472,491 A | 12/1995 | Duschek et al. |
| 5,500,223 A | 3/1996 | Behan et al. |
| 5,520,917 A | 5/1996 | Mizuguchi et al. |
| 5,556,617 A | 9/1996 | Ribier et al. |
| 5,587,170 A | 12/1996 | Caisey et al. |
| 5,591,453 A | 1/1997 | Ducheyne et al. |
| 5,607,664 A | 3/1997 | Ascione et al. |
| 5,632,996 A | 5/1997 | Ramirez et al. |
| 5,635,809 A | 6/1997 | Ganser et al. |
| 5,650,311 A | 7/1997 | Avnir et al. |
| 5,670,209 A | 9/1997 | Wyckoff |
| 5,672,301 A | 9/1997 | Orly et al. |
| 5,691,060 A | 11/1997 | Levy et al. |

(Continued)

FOREIGN PATENT DOCUMENTS

| | | |
|---|---|---|
| AU | 764016 B2 | 8/2003 |
| AU | 199963469 B2 | 8/2003 |

(Continued)

OTHER PUBLICATIONS

Lotion crafter http://www.lotioncrafter.com/dimethyl-isosorbide-dmi.html.*
Cutis Benzoyl Peroxide Rosacea Study Summary, 2010, http://www.rosacea-treatment-clinic.com.au/Benzoyl-Peroxide/Benzoyl-Peroxide-Acetone.html.*
Benzoyl Peroxide ("BPO", Chem and Tech. Assess. 2004, 61st JECFA, 1-6, http://www.fao.org/fileadmin/templates/agns/pdf/jecfa/cta/63/Benzoylperoxide.pdf).*

(Continued)

*Primary Examiner* — Anoop Singh
*Assistant Examiner* — Doan Phan
(74) *Attorney, Agent, or Firm* — Browdy and Neimark, PLLC

(57) ABSTRACT

The present invention relates to pharmaceutical compositions for topical use (including also dermatological compositions), for treating skin conditions and afflictions, such as rosacea and symptoms and conditions associated there from.

12 Claims, 3 Drawing Sheets

(56) References Cited

U.S. PATENT DOCUMENTS

| | | |
|---|---|---|
| 5,700,451 A | 12/1997 | Yue et al. |
| 5,733,531 A | 3/1998 | Mitchnick et al. |
| 5,739,020 A | 4/1998 | Pope |
| 5,767,098 A | 6/1998 | Klein |
| 5,785,977 A | 7/1998 | Breithbarth |
| 5,792,250 A | 8/1998 | Braun et al. |
| 5,851,538 A | 12/1998 | Froix et al. |
| 5,874,105 A | 2/1999 | Watkins et al. |
| 5,876,699 A | 3/1999 | DiSomma et al. |
| 5,879,716 A | 3/1999 | Katz et al. |
| 5,895,757 A | 4/1999 | Pope |
| 5,906,811 A | 5/1999 | Hersh |
| 5,912,016 A | 6/1999 | Perrier et al. |
| 5,914,101 A | 6/1999 | Tapley et al. |
| 5,914,104 A | 6/1999 | Moore |
| 5,932,228 A | 8/1999 | Hall et al. |
| 5,955,109 A | 9/1999 | Won et al. |
| 5,962,517 A | 10/1999 | Murad |
| 5,998,392 A | 12/1999 | Simard et al. |
| 6,013,637 A | 1/2000 | Klein et al. |
| 6,015,548 A | 1/2000 | Siddiqui et al. |
| 6,074,629 A | 6/2000 | Kostinko et al. |
| 6,077,522 A | 6/2000 | Scher et al. |
| 6,090,399 A | 7/2000 | Ghosh et al. |
| 6,096,765 A | 8/2000 | Bershad |
| 6,103,267 A | 8/2000 | Mitchnick et al. |
| 6,117,843 A | 9/2000 | Baroody et al. |
| 6,132,773 A | 10/2000 | Amiche |
| 6,143,280 A | 11/2000 | Pike et al. |
| 6,146,664 A | 11/2000 | Siddiqui |
| 6,159,453 A | 12/2000 | Avnir et al. |
| 6,171,600 B1 | 1/2001 | Dahms |
| 6,197,757 B1 | 3/2001 | Perrier et al. |
| 6,200,375 B1 | 3/2001 | Guez et al. |
| 6,217,852 B1 | 4/2001 | Gildenberg et al. |
| 6,238,650 B1 | 5/2001 | Lapidot et al. |
| 6,242,099 B1 | 6/2001 | Grandmontagne et al. |
| 6,251,313 B1 | 6/2001 | Deubzer et al. |
| 6,280,746 B1 | 8/2001 | Arquette et al. |
| 6,303,149 B1 | 10/2001 | Magdassi et al. |
| 6,303,290 B1 | 10/2001 | Liu et al. |
| 6,337,089 B1 | 1/2002 | Yoshioka et al. |
| 6,436,375 B1 | 8/2002 | Lapidot et al. |
| 6,468,509 B2 | 10/2002 | Lapidot et al. |
| 6,479,146 B1 | 11/2002 | Caruso et al. |
| 6,495,352 B1 | 12/2002 | Brinker et al. |
| 6,534,044 B1 | 3/2003 | Wada et al. |
| 6,537,583 B1 | 3/2003 | Dupuis et al. |
| 6,607,713 B1 | 8/2003 | Chodorowski et al. |
| 6,616,947 B1 | 9/2003 | Depuis |
| 6,703,032 B2 | 3/2004 | Gers-Barlag et al. |
| 6,855,335 B2 | 2/2005 | Seok et al. |
| 6,875,264 B2 | 4/2005 | Zimmermann et al. |
| 6,913,825 B2 | 7/2005 | Ostafin et al. |
| 7,001,592 B1 | 2/2006 | Traynor et al. |
| 7,037,513 B1 | 5/2006 | Traynor et al. |
| 7,052,913 B2 | 5/2006 | Babich et al. |
| 7,758,888 B2 | 7/2010 | Lapidot et al. |
| 8,039,020 B2 * | 10/2011 | Lapidot et al. ............... 424/489 |
| 8,568,704 B2 | 10/2013 | Mallard |
| 2002/0064541 A1 | 5/2002 | Lapidot et al. |
| 2002/0151527 A1 | 10/2002 | Wiegand et al. |
| 2002/0193321 A1 | 12/2002 | Vishnupad et al. |
| 2003/0004118 A1 | 1/2003 | Vishnupad et al. |
| 2003/0157330 A1 | 8/2003 | Ostafin et al. |
| 2003/0170196 A1 | 9/2003 | Orsoni et al. |
| 2004/0101566 A1 | 5/2004 | Cooper et al. |
| 2004/0157766 A1 | 8/2004 | Embil et al. |
| 2005/0037087 A1 | 2/2005 | Lapidot et al. |
| 2005/0208134 A1 | 9/2005 | Magdassi et al. |
| 2005/0276807 A1 | 12/2005 | Skurkovich et al. |
| 2006/0128808 A1 | 6/2006 | Arsonnaud et al. |
| 2006/0204530 A1 * | 9/2006 | Ramirez et al. ............... 424/401 |
| 2006/0251687 A1 | 11/2006 | Lapidot et al. |
| 2006/0292093 A1 * | 12/2006 | Carola ................... A61K 8/498 424/59 |
| 2007/0003585 A1 | 1/2007 | Clark et al. |
| 2007/0292676 A1 | 12/2007 | Naigertsik et al. |
| 2008/0292560 A1 * | 11/2008 | Tamarkin et al. ............... 424/45 |
| 2009/0081262 A1 | 3/2009 | Toledano et al. |
| 2010/0047357 A1 | 2/2010 | Toledano et al. |
| 2010/0143285 A1 | 6/2010 | Mallard et al. |
| 2011/0052515 A1 | 3/2011 | Kaoukhov et al. |
| 2011/0177951 A1 * | 7/2011 | Toledano et al. ............. 504/342 |
| 2011/0237555 A1 | 9/2011 | Sanchez et al. |
| 2012/0015014 A1 | 1/2012 | Lapidot et al. |
| 2012/0064135 A1 | 3/2012 | Levin et al. |
| 2012/0269874 A1 | 10/2012 | Toledano et al. |
| 2013/0095185 A1 * | 4/2013 | Toledano ............. A61K 9/0014 424/490 |

FOREIGN PATENT DOCUMENTS

| | | |
|---|---|---|
| CN | 101605537 A | 12/2009 |
| DE | 4416003 A1 | 11/1995 |
| DE | 19811900 A1 | 9/1999 |
| DE | 202011100767 U1 | 12/2011 |
| EP | 0281034 A2 | 9/1988 |
| EP | 0 462 388 A2 | 12/1991 |
| EP | 0 478 326 A1 | 4/1992 |
| EP | 0 581 651 A2 | 2/1994 |
| EP | 0680753 A2 | 11/1995 |
| EP | 0 934 773 A2 | 8/1999 |
| EP | 0941761 A2 | 9/1999 |
| EP | 0972563 A1 | 1/2000 |
| EP | 1116516 A1 | 7/2001 |
| FR | 2703927 A1 | 10/1994 |
| FR | 2774906 A1 | 8/1999 |
| FR | 2780901 A1 | 1/2000 |
| GB | 1399344 A | 7/1975 |
| GB | 2416524 A | 2/2006 |
| JP | 01-113436 A | 5/1989 |
| JP | 2040302 A | 2/1990 |
| JP | 02-251240 A | 10/1990 |
| JP | 03-229634 A | 10/1991 |
| JP | 03-243663 A | 10/1991 |
| JP | 07173452 A | 7/1995 |
| JP | 09110463 A | 4/1997 |
| JP | 09-235217 A | 9/1997 |
| JP | 02-002867 A2 | 1/2002 |
| JP | 02-292824 A | 10/2002 |
| JP | 03-534249 A | 11/2003 |
| JP | 05-043208 A | 2/2005 |
| JP | 05-513146 A | 5/2005 |
| JP | 05-528152 A | 9/2005 |
| JP | 05-529636 A | 10/2005 |
| RU | 98105780 A2 | 12/1999 |
| RU | 2314093 C2 | 1/2008 |
| WO | 94/04260 A1 | 3/1994 |
| WO | 94/04261 A1 | 3/1994 |
| WO | 9707676 A1 | 3/1997 |
| WO | 97/32561 A1 | 9/1997 |
| WO | 97/40106 A1 | 10/1997 |
| WO | 97/45367 A1 | 12/1997 |
| WO | 98/15183 A1 | 4/1998 |
| WO | 98/31333 A1 | 7/1998 |
| WO | 99/03450 A1 | 1/1999 |
| WO | 0009652 A2 | 2/2000 |
| WO | 0025761 A1 | 5/2000 |
| WO | 0025908 A1 | 5/2000 |
| WO | 0047236 A1 | 8/2000 |
| WO | 0071084 A | 11/2000 |
| WO | 0072806 A2 | 12/2000 |
| WO | 0112221 A1 | 2/2001 |
| WO | 0113924 A2 | 3/2001 |
| WO | 01/58451 A1 | 8/2001 |
| WO | 0180823 A2 | 11/2001 |
| WO | 02/085113 A1 | 10/2002 |
| WO | 03/003497 A1 | 1/2003 |
| WO | 03/034973 A1 | 5/2003 |
| WO | 03/039510 A1 | 5/2003 |
| WO | 03/066209 A1 | 8/2003 |
| WO | 03/086419 A1 | 10/2003 |

(56) References Cited

FOREIGN PATENT DOCUMENTS

| | | |
|---|---|---|
| WO | 03104319 A1 | 12/2003 |
| WO | 2004/064769 A2 | 8/2004 |
| WO | 2004/064803 A1 | 8/2004 |
| WO | 2004/069135 A2 | 8/2004 |
| WO | 2004/069216 A1 | 8/2004 |
| WO | 2004/81222 A2 | 9/2004 |
| WO | 2005009604 A1 | 2/2005 |
| WO | 2007/000316 A1 | 1/2007 |
| WO | 2007/015243 A2 | 2/2007 |
| WO | 2007/036939 A2 | 4/2007 |
| WO | 2008/002637 A2 | 1/2008 |
| WO | 2008/057411 A1 | 5/2008 |
| WO | 2008/093346 A2 | 8/2008 |
| WO | 2008/093347 A1 | 8/2008 |
| WO | 2009/148584 A1 | 12/2009 |
| WO | 2011/049547 A1 | 4/2011 |
| WO | 2012037000 A1 | 3/2012 |

OTHER PUBLICATIONS

"Environmental Protection Agency", Federal Register, 2002, vol. 67, No. 94 and 40 CFR part 180, pp. 34616-34620. Federal Register vol. 67, No. 94 and 40 CFR part 180, May 15, 2002/Rules and Regulations, pp. 34616-34620.
"Ludox TM-50 colloidal silica," Sigma-Aldrich website: http://www.sigmaaaldrich.com/catalog/product/aldrich/420778?lang=en&region=US, downloaded Sep. 7, 2012.
"Martindale: The extra Pharmacopeia," Pharmaceutical Press, pp. 1093-1095, 1999.
Aizawa et al., "Preparation of Spherical Hydrous Silica Oxide Particles under Acidic Condition via Sol-Gel Processing", Journal of Sol-Gel Science and Technology, 19:329-332(2000).
Bashir and Maibach, The Chemistry and Manufacture of Cosmetics V1 Chapter 5 third ed. pp. 163-182 (2000).
Beelen et al., "The Role of Aging on the Formation of Porous Silica," Preparation of Catalysts VI, pp. 33-48, Elsevier Science B.V. (1995).
Breneman et al. "Double-blind, randomized, vehicle-controlled clinical trial of once-daily benzoyl peroxide/clindamycin topical gel in the treatment of patients with moderate to severe rosacea" (Int. J. Derma. 43, 381-387 (2004).
Brinker et al. "Sol-Gel Science, The Physics and Chemistry of Sol-Gel Processing" Academic Press, Inc., San Diego, CA, pp. 104-105, 134-137, 146-147, 150-151 and 562-563. (1990).
Bugnon, P., "Surface treatment of pigments. Treatment with inorganic materials", Progress in Organic Coatings, 29:39-43 (1996).
Bugosh, "Colloidal Alumina—The Chemistry and Morphology of Colloidal Boehmite", Chemistry and Morphology of Colloidal Boehmite, 65:1789-1793 (1961).
Butler et al., "An emulsion method for producing fine, low density, high surface area silica powder from alkoxides", Journal of Materials Science, 31:1675-1680 (1996).
Chung et al., "Aqueous Synthesis of Y2O2S: Eu/Silica Core-Shell Particles", Journal of the American Ceramic Society, 88(5):1341-1344 (2005).
Dun et al., "Layer-by-Layer Self-Assembly of Multilayer Zirconia Nanoparticles on Silica Spheres for HPLC Packings", Analytical Chemistry, 76(17):5016-5023 (2004).
Fireman et al., "A Look at emerging delivery systems for topical drug products" Derma. Ther. 24:477-488 (2011).
Hall, S., et al., "Cocondensation of Organosilica Hybrid Shells on Nanoparticle, Templates: A Direct Synthetic Route to Functionalized Core-Shell Colloids", Langmuir, 16:1454-1456 (2000).
Haq et al., "Preparation and properties of uniform coated inorganic colloidal particles 9. Titania on copper compounds", Colloids and Surfaces A: Physicochemical and Engineering Aspects, 81:153-159 (1993).
Hench, et al., "The Sol-Gel Process", Chem. Rev. 90, pp. 33-72 (1990).
Hsu et al., "Paper Whiteners", Journal of Colloid and Interface Science, 156(1):56-65 (1993).
Iler Ralph K., The Chemistry of Silica, Wiley-Interscience publication, 510-533 (1979).
Iler Ralph K, "The Chemistry of Silica, Solubility, Polymerization, Colloid and Surface Properties, and Biochemistry," John Wiley & Sons, pp. 366-367 (1979).
International Search Report dated Apr. 16, 1999, for PCT/IL2008/000140 (WO2008/093346 A3).
Iskandar et al., "Control of the morphology of nanostructured particles prepared by the spray drying of a nanoparticle sol", Journal of Colloid and Interface Science, 265:296-303 (2003).
Iskandar et al., "Preparation of microencapsulated powders by an aerosol spray method and their optical properties", Advanced Powder Technol., 14(3):349-367 (2003).
James J. Leyden, Comparison of the Efficacy and Safety of a Combination Topical Gel Formulation of Benzoyl Peroxide and Clindamycin with Benzoyl Peroxide, Clindamycin and Vehicle Gel in the Treatments of Acne Vulgaris, Am J Clin Dermatol 2(1): 33-39 (2001).
Jean et al., "Y2O2S:Eu Red Phosphor Powders Coated with Silica", Journal of the American Ceramic Society, 83(8):1928-34 (2000).
Kim et al., "Monodisperse hollow titania nanospheres prepared using a cationic colloidal template", Journal of Colloid and Interface Science, 304(2):370-377 (2006).
Kortesuo et al., "Effect of synthesis parameters of the sol-gel-processed spray-dried silica gel microparticles on the release rate of dexmedetomidine", Biomaterials, 23:2795-2801 (2002).
Kortesuo et al., "In vitro evaluation of sol-gel processed spray dried silica gel microspheres as carrier in controlled drug delivery", International Journal of Pharmaceutics, 200:223-229 (2000).
Lapidot, et al., "Advanced Sunscreens: UV Absorbers Encapsulated in Sol-Gel Glass Microcapsules", Journal of Sol-Gel Science and Technology, 26:67-72 (2003).
Liz-Marzan et al., "Synthesis of Nanosized Gold-Silica Core-Shell Particles," Langmuir, 12:4329-4335 (1996).
Maibach., "Reduction of Skin Irritancy with Microsponge® Topical Delivery" Aesthetic Dermatology, Touch Briefings, pp. 45-47 (2008).
Makarova et al., "Adsorption and Encapsulation of Fluorescent Probes in Nanoparticles", J. Phys. Chem. B, American Chemical Society, 103(43):9080-9084 (1999).
Hardikar et al., "Coating of Nanosize Silver Particles with Silica", Journal of Colloid and Interface Science, 221(1):133-136 (2000).
Merikhi et al., "Adhesion of Colloidal SiO2 Particles on ZnS-Type Phosphor Surfaces", Journal of Colloid and Interface Science, 228:121-126 (2000).
Mikrajuddin et al., "Stable photoluminescence of zinc oxide quantum dots in silica nanoparticles matrix prepared by the combined sol-gel and spray drying method", Journal of Applied Physics, 89(11):6431-6434 (2001).
Montes et al., "Topical Treatment of Acne Rosacea with Benzoyl Peroxide Acetone Gel" Cutis 32:185-190 (1983).
Nakatsuka, "Surface Modification of Inorganic Pigments with Organic UV Absorbers", Colloids and Surfaces, 34:323-334 (1988/89).
Nokhodchi, Iranian J. of Pharmaceutical Sciences, Summer 2005: 1(3): 131-142 (2005).
Rottman, C., et al., "Advanced Sunscreens: UV Absorbers Entrapped in Glass Microcapsules", Euro Cosmetics, pp. 20-22, (2000).
Rottman et al., "Advanced Sunscreens: UV Absorbers Entrapped in Sol-Gel Glass Microcapsules", Journal of Sol-Gel Science and Technology, 23:268-270 (2002).
Stober process from Wikipedia, http://en.wikipedia.org/wiki/St%C3%B6ber_process, downloaded May 8, 2013.
Takeuchi et al., "Solid dispersion particles of tolbutamide prepared with fine silica particles by the spray-drying method", Powder Technology, 141:187-195 (2004).
Tatapudy et al., "Benzyl Peroxide Microcapsules I. Preparation of Core Material", Indian Drugs, 32(6):239-248 (1995).
Van Bruggen, et al., "Preparation and Properties of Colloidal Core-Shell Rods with Adjustable Aspect Ratios", Langmuir, 14(9):2245-2255 (1998).

(56) References Cited

OTHER PUBLICATIONS

Villalobos et al., "Protective Silica Coatings on Zinc-Sulfide-Based Phosphor Particles", Journal of the American Ceramic Society, 85(8):2128-2130 (2002).
Wang et al., "Effect of Polyelectrolyte Dispersants on the Preparation of Silica-Coated Zinc Oxide Particles in Aqueous Media", Journal of the American Ceramic Society,85(8):1937-1940 (2002).
Wenninger et al., "International Cosmetic Ingredient Dictionary and Handbook", 2:1140-1147 (2000).
Wester et al., "Controlled release of benzoyl peroxide from a porous microsphere polymeric system can reduce topical irritancy" J. Am. Acad. Derma. 24:720-726 (1991).
Wilhelm et al., "On-line tracking of the coating of nanoscaled silica with titania nanoparticles via zeta-potential measurements", Journal of Colloid and Interface Science, 293:88-92 (2006).
Yamasaki et al., "Increased serine protease activity and cathelicidin promotes skin inflammation in rosacea" Nature Medicine (13)(8):975-980 (Aug. 2007).
Yuan et al., "Organic Pigment Particles Coated with Colloidal Nano-Silica Particles via Layer-by-Layer Assembly", Chem. Mater., 17(14):3587-3594 (2005).
Zhu-Zhu Li et al., "Fabrication of Porous Hollow Silica Nanoparticles and Their Applications in Drug Release Control," Journal of Controlled Release, 98:245-254 (2004).
Tissot et al., "Hybrid Latex Particles Coated with Silica" Macromolecules 34:5737-5739 (2001).
Wenninger et al., "International Cosmetic Ingredient Dictionary and Handbook" vol. 2, Seventh Edition, pp. 1656-1662 (1997).
Sreco et al "Preparation and coating of finely dispersed drugs 4. Loratadine and danazol" Journal of Colloid and Interface Science. 272:90-98 (2004).
Tjandra et al "Interaction between Silicates and Ionic Surfactants in Dilute Solution" Langmuir. 22:1493-1499 (2006).
The Extra Pharmaceutical Necessities, M. Luo, T. Gao, 1993, Sicuan Academic Press, Chendu, pp. 23-28.

\* cited by examiner

COMPOSITIONS FOR THE TREATMENT OF ROSACEA

TECHNOLOGICAL FIELD

This invention relates to pharmaceutical compositions for topical use (including also dermatological compositions), for treating skin conditions and afflictions, such as rosacea and symptoms and conditions associated there from.

BACKGROUND

Rosacea is a chronic disease of inflammatory dermatitis that mainly affects the median part of the face and the eyelids of certain adults. It is characterized by telangiectatic erythema, dryness of the skin, papules and pustules. Conventionally, rosacea develops in adults from the ages of 30 to 50; it more frequently affects women, although the condition is generally more severe in men. Rosacea is a primitively vascular condition whose inflammatory stage lacks the cysts and comedones characteristic of common acne.

Factors that have been described as possibly contributing towards the development of rosacea include for example: the presence of parasites such as the *Demodex folliculorum*, the presence of bacteria such as *Helicobacter pylori* (a bacterium associated with gastrointestinal disorders), hormonal factors (such as endocrine factors), climatic and immunological factors, and so forth.

Rosacea develops in four stages over several years, in spasms aggravated by variations in temperature, alcohol, spices, exposure to sunlight and stress.

The various stages of the disease are the following:

Stage 1: stage of erythema episodes. The patients have erythrosis spasms due to the sudden dilation of the arterioles of the face, which then take on a congestive, red appearance. These spasms are caused by the emotions, meals and temperature changes.

Stage 2: stage of couperosis, i.e., of permanent erythema with telangiectasia. Certain patients also have oedema on the cheeks and the forehead.

Stage 3: inflammatory stage (papularpostular rosacea) with appearance of inflammatory papules and pustules, but without affecting the sebaceous follicles and thus with absence of cysts and comedones.

Stage 4: rhinophyma stage. This late phase essentially affects men. The patients have a bumpy, voluminous red nose with sebaceous hyperplasia and fibrous reordering of the connective tissue.

Typical treatment of rosacea include oral or topical administration of antibiotics such as tetracyclines, salicylic acid, anti-fungal agents, steroids, metronidazole (an antibacterial agent) or with isotretinoin in severe cases, or even with anti-infectious agents such as azelaic acid.

US 20110052515 described a pharmaceutical/dermatological topically applicable formulation for treating rosacea, comprising at least one avermectin compound and benzoyl peroxide (BPO, an anti-acne agent).

Breneman et al. (*Int. J. Derma.* 43, 381-387 (2004)) reported the results of a double blind randomized vehicle-controlled clinical trial of once-daily BPO and clindamycin topical gel in the treatment of moderate to severe rosacea.

Montes et al. (*Cutis,* 32, 185-190 (1983)) disclosed the use of BPO dissolved in acetone gel formulation for the treatment of rosacea.

Wester et al. (*J. Am. Acad. Derma.* 24, 720-726 (1991)) related to the controlled release of BPO from porous microsphere polymeric systems in the treatment of acne.

These previous rosacea treatments with BPO alone or in combination with other agents, have been shown to have severe drawbacks such as irritation and intolerance phenomena, especially when they are administered for a prolonged period. On the other hand, these treatments are only suppressive and not curative, acting especially on the pustulous spasms occurring during the inflammatory stage.

Considering the chronic nature of rosacea, there is a need for a prolonged use treatment of the disease, its symptoms and associated conditions, in a safe and effective manner. Thus, there exists a need for compositions that show improved efficacy in the treatment of rosacea, that impart greater tolerance to the active principles and that do not have the side effects described in the prior art.

GENERAL DESCRIPTION

Accordingly, the present invention provides a composition comprising benzoyl peroxide for topical use in the treatment of rosacea, wherein said benzoyl peroxide is in a solid form.

In some embodiments said BPO comprises between about 2.5 weight % to about 5 weight % of the composition. In some embodiments the BPO is the single pharmaceutical active agent in the composition. In other embodiments the composition further comprises a further active agent (pharmaceutical active agent or a cosmetically active agent).

The term "topical use" is meant to encompass the topical administration of a composition of the invention by formulating said composition in any way known in the art, or in formulations disclosed herein, which are compatible with the skin, mucous membranes and/or the integuments.

The invention further provides a composition comprising benzoyl peroxide for topical use in the treatment of rosacea, wherein the dissolution rate of the benzoyl peroxide from composition is less than about 80% weight/h. In some embodiments of this aspect, said benzoyl peroxide is the single pharmaceutical active agent in said composition.

In some embodiments, said dissolution rate is between about 20% weight/h to about 80% weight/h. In other embodiments, said dissolution rate is between about 40 to 60% weight/h. In yet other embodiments, said dissolution rate is less than about 40% weight/h. In further embodiments said dissolution rate is less than about 20% weight/h. In some further embodiments said dissolution rate is between about 10% weight/h to about 50 weight %/h (i.e. 10, 15, 20, 25, 30, 35, 40, 45, 50%/h).

In the context of the present invention the term "dissolution rate" relates to the rate in weight per time units of dissolution of solid BPO from the composition of the invention to the surrounding immediate environment. The dissolution rate as disclosed in the present application is measured as disclosed in Example 5 below.

The invention further provides a composition comprising benzoyl peroxide for topical use in the treatment of rosacea, wherein the dissolution rate of the benzoyl peroxide from composition is less than about 40 mg/h.

It has been found by the inventors of the present application that a composition comprising BPO, having dissolution rate of less than about 80%/h provides a safer and more effective treatment of rosacea with respect to the tolerance and adverse effect as compared with compositions having similar amount of pharmaceutical active agent with faster dissolution. It was shown by the inventors of the application that as the dissolution rate of BPO is lowered to less than 80%/h the treatment of a chronic skin disease such as rosacea, including its symptoms and conditions associated therewith, was dramatically improved since the controlled release of the pharmaceutical active agent was slow enough to allow for controlled and slow release of the pharmaceutical active agent over a prolonged period of time, releasing an amount of BPO able to treat the disease, symptoms and/or conditions associated with rosacea, but on the other hand not allowing for intolerance or adverse effects to appear. In some embodiments when the composition comprises BPO as a single pharmaceutical active agent, treatment results of rosacea were comparable to the compositions know in the art comprising BPO and an antibacterial agent.

The present invention discloses pharmaceutical compositions, including dermatological compositions, comprising benzoyl peroxide as a single pharmaceutical active agent in the solid form. In some embodiments said compositions are formulated into a physiologically acceptable form.

In further embodiments a composition of the invention may comprise at least one further pharmaceutical active agent (in addition to the BPO).

In some embodiments a composition of the invention comprises at least one further pharmaceutical active agent selected from the group consisting of an antibiotic agent, a tetracycline agent, a retinoid, an antimicrobial agent and any combinations thereof.

In some embodiments said at least one further pharmaceutical active agent is selected from the following non-limiting list: Antibiotics such as clindamycin or erythromycin. Tetracyclines such as minocycline or doxycycline. Retinoids and other compounds that bind to and activates the RAR and/or RXR receptors such as all trans retinoic acid (tretinoin), tazarotene, adapalene, a acitretin, 13 cis retinoic acid (isotretinoin), 9 cis retinoic acid (alitretinoin) or betaxorene and their metabolic and chemical derivatives. Antimicrobial agents such as metronidazole, sodium sulfacetamide-sulfur or azaleic acid, α-adrenergic receptor agonist such as brimonidine, oxymetazoline, naphazoline, tetrahydrozoline, xylometazoline, phenylephrine, methoxamine, mephentermine, metaraminol, midodrine, epinephrine, clonidine or norepinephrine.

Under such embodiments, at least one of said at least one further pharmaceutical active agent and/or said BPO are encapsulated in a microcapsule.

This invention also features compositions formulated as medicaments for improving, preventing and/or treating a skin condition, notably rosacea, and which substantially reduce the duration of the treatment and which provide a greater reduction of the symptoms of rosacea.

In some embodiments, said benzoyl peroxide is present in the composition in an amount of at least about 1.0% by weight of said composition.

In some further embodiments, said benzoyl peroxide is present in the composition in an amount between about 2.5% to about 10% by weight of said composition. In further embodiments said benzoyl peroxide is present in the composition in an amount of between about 2.5% to about 5% by weight of said composition.

In further embodiments, said benzoyl peroxide is in a crystalline form.

In some embodiments, said rosacea is papularpostular rosacea (i.e. inflammatory rosacea, see Rapini, Ronald P. et al. (2007). *Dermatology:* 2-Volume Set. St. Louis: Mosby and James, William et al. (2005). *Andrews' Diseases of the Skin: Clinical Dermatology*. (10th ed.). Saunders p. 245).

In other embodiments, said composition of the invention demonstrates adverse events value of no more than about (less than about) 50% upon topical use in the treatment of rosacea. In some embodiments wherein said composition demonstrates adverse events values of no more than about (less than about) 40%, 30%, 20% upon topical use in the treatment of rosacea.

The term "adverse events values" refers to average percentage of subjects that experience any adverse events associated with the treatment of rosacea with a composition of the invention (usually on the skin of a subject treated with a composition of the invention). A non-limiting list of such adverse events includes: irritation, dryness, scaling, purities, burning and stinging.

A composition of the invention was shown to demonstrate a high percentage of subjects having a 2-grade improvement in the IGA (Investigator General Assessment) and reached a clear or almost clear condition of the disease, relative to baseline, at week 12.

In some embodiments said 2-grade improvement in the IGA was between about 20% to about 80%, in some other embodiments 30% to 70%, in some further embodiments 40-60%.

The term "dissolution rate of BPO from composition" refers to the quantitative amount of BPO dissolved from the composition of the invention in units of mg of BPO per time (h).

It is to be understood that the inventors of the present application have surprisingly found that a controlled dissolution rate of less than about 80% weight/h of BPO from a composition of the invention provides a safe, tolerable and effective treatment of a chronic skin disease such as rosacea, causing minimal adverse effects upon prolonged use of the skin.

In some further embodiments, a composition of the invention further comprises at least one non pharmaceutical active additive selected from the group consisting of chelating agents, antioxidants, sunscreens, preservatives, fillers, electrolytes, humectants, dyes, mineral or organic acids or bases, fragrances, essential oils, moisturizers, vitamins, essential fatty acids, sphingolipids, self-tanning compounds, calmatives and skin-protecting agents, pro-penetrating agents and gelling agents, or a mixture thereof.

In other embodiments, a composition of the invention is formulated into a topically applicable, physiologically acceptable medium consisting of: (a) at least one member selected from the group consisting of water, alcohols, oils, fatty substances and waxes; and (b) at least one additive selected from the group consisting of chelating agents, antioxidants, sunscreens, preservatives, fillers, electrolytes, humectants, dyes, mineral acids, mineral bases, organic acids, organic bases, fragrances, essential oils, moisturizers, vitamins, essential fatty acids, sphingolipids, self-tanning compounds, calmatives, skin-protecting agents, pro-penetrating agents, gelling agents, emulsifiers, co-emulsifiers, and mixtures thereof.

In some embodiments a composition of the invention is formulated to an emulsion (including an oil-in-water emulsion, a water-in-oil emulsion, multiple emulsions and microemulsions). In other embodiments a composition of the invention is formulated to a cream. In further embodiments, a composition of the invention is formulated to a gel.

The compositions according to the invention are pharmaceutical compositions, and especially dermatological compositions, which may be in any galenical form conventionally used for topical application and especially in the form of aqueous gels, and aqueous or aqueous-alcoholic solutions. By addition of a fatty or oily phase, it may also be in the form of dispersions of the lotion or serum type, emulsions of liquid or semi-liquid consistency of the milk type obtained by dispersing a fatty phase in an aqueous phase (O/W) or conversely (W/O), or suspensions or emulsions of soft, semi-liquid or solid consistency of the cream, gel or ointment type, or alternatively multiple emulsions (W/O/W or O/W/O), microemulsions, microcapsules, microparticles or vesicular dispersions of ionic and/or nonionic type, or wax/aqueous phase dispersions. These compositions are formulated according to the usual methods.

In further embodiments, a composition of the invention comprising, as a single pharmaceutical active agent, benzoyl peroxide in a solid form, for topical use in the treatment of rosacea, is an oil in water emulsion comprising a polyoxylstearate and a glycerylstearate.

In some embodiments the ratio of said polyoxylstearate to said glycerylstearate is in the range of 0.1:10 to 10:0.1.

In yet further embodiments, said polyoxylstearate is selected from the group consisting of Polyoxyl-8 stearate, Polyoxyl-20 stearate, Polyoxyl-40 stearate, and Polyoxyl-100 stearate.

In further embodiments, said glycerylstearate is selected from the group consisting of glyceryl mono-stearate, glyceryl di-stearate and mixtures thereof.

In other embodiments, said polyoxylstearate in said composition is in the range of about 0.1% w/w to about 30% w/w.

In further embodiments, the amount of said glycerylstearate in said composition is in the range of about 0.1% w/w to about 30% w/w.

In other embodiments, said composition further comprises at least one fatty alcohol.

In other embodiments, said at least one fatty alcohol is selected from the group consisting of octyl alcohol, 2-ethyl hexanol, nonyl alcohol, decyl alcohol, undecanol, dodecyl alcohol, tridecyl alcohol, tetradecyl alcohol, pentadecyl alcohol, cetyl alcohol, palmitoleyl alcohol, heptadecyl alcohol, cetostearyl alcohol, stearyl alcohol, isostearyl alcohol, elaidyl alcohol, oleyl alcohol, linoleyl alcohol, elaidolinolenyl alcohol, ricinoleyl alcohol, nonadecyl alcohol, arachidyl alcohol, heneicosyl alcohol, behenyl alcohol, erucyl alcohol, lignoceryl alcohol, ceryl alcohol, montanyl alcohol, cluytyl alcohol, myricyl alcohol, melissyl alcohol, geddyl alcohol, cetearyl alcohol and mixtures thereof.

In further embodiments, the amount of said at least one fatty alcohol in said composition is in the range of about 0.2% w/w to about 50% w/w.

In yet other embodiments, said composition further comprises a polyacrylic acid homopolymer or copolymer.

In other embodiments, said oil in said oil in water emulsion is selected from the group consisting of paraffin oil, isopropyl myristate, caprylic/capric triglyceride, squalane, squalene, almond oil, castor oil, olive oil, jojoba oil, sunflower oil, soybean oil, grape seed oil, dimethicone, cyclomethicone and mixtures thereof.

In further embodiments, said oil in present in the composition in an amount in the range of about 0.05% w/w to about 50% w/w.

In some embodiments, said water in said oil in water emulsion further comprises at least one water soluble humectant.

In other embodiments, said at least one water soluble humectant is selected from the group consisting of propylene glycol, glycerin, and polyethylene glycol-X, where X is in the range of 200 to 10,000.

In yet other embodiments, a composition of the invention comprising, as a single pharmaceutical active agent, benzoyl peroxide in a solid form, for topical use in the treatment of rosacea, is in a gel form comprising at least one non-ionic polymeric dispersant and at least one thickening agent.

In some embodiments, said at least one non-ionic polymeric dispersant is selected from the group consisting of poly vinyl pyrrolidone (PVP), poly vinyl pyrrolidone-co-vinyl acetate, polyamide, polyurethane, polyurea and mixtures thereof.

In some further embodiments, said at least one thickening agent is selected from the group consisting of hydroxy propyl cellulose (HPC), hydroxyl ethyl cellulose (HEC), hydroxyl methyl cellulose (HMC), polyacrylic acid homopolymer, polyacrylic acid copolymer, fatty alcohol, silica and its derivatives, xanthan gum, arabic gum, poly vinyl alcohol, veegum, laponite, clay, and mixtures thereof.

In other embodiments, said at least one thickening agent is a non-ionic agent.

In further embodiments, said at least one thickening agent is an ionic agent.

In other embodiments, said at least one thickening agent is present in the composition in an amount in the range of about 0.01% w/w to about 10% w/w.

In further embodiments, said composition further comprises glycerin.

In other embodiments, said non-ionic polymeric dispersant is present in the composition in an amount in the range of about 0.05% w/w to about 20% w/w.

In some embodiments, said composition of the invention comprises said solid BPO is in a controlled release drug delivery system.

In further embodiments, said controlled or slowed release drug delivery system is an encapsulation in a microcapsule, wherein said solid BPO is embedded in said microcapsule.

When referring to a "controlled or slowed release drug delivery system" it should be understood to relate to a delivery system (which in the present invention is a topical delivery system) that enables the release of the pharmaceutical active agent in predetermined amounts over a specified period. In some embodiments said system is a core-shell system of a microcapsule or a porous matrix structure, such as for example a microsponge.

The term "embedded" should be understood to encompass an inert system that provides a barrier between the pharmaceutical active agent, i.e. BPO, and its surrounding environment in the composition. In some embodiments said agent is entrapped and/or encapsulated in said controlled release system.

In some embodiments said core of said microcapsule consists of said solid BPO.

In some further embodiments, said microcapsules are a core shell microcapsule. The shell comprises at least one inorganic polymer. In some other embodiments, said inorganic polymer of said shell is a metal oxide or semi-metal oxide shell (layer).

In some embodiments of the invention said microcapsule consists of a metal oxide or semi-metal oxide coating or layer (shell) and a core consisting of solid BPO.

In some embodiments said microcapsule consisting of a metal oxide or semi-metal oxide coating or layer (shell) and a core consisting of solid BPO is prepared by a process comprising the steps of:

(a) contacting a solid BPO particulate matter with an ionic additive and an aqueous medium to obtain a dispersion of said particulate matter having positive charges on its surface;

(b) subjecting the particulate matter to a coating procedure comprising precipitating a metal oxide salt onto the surface of the particulate matter to form a metal oxide layer thereon thereby to obtain particulate matter coated by a metal oxide coating layer;

(c) repeating step (b) at least 4 more times; and (d) aging said coating layer.

As used herein the term "solid BPO particulate matter" refers to a solid BPO having solubility in water of less than 1% w/w, typically less than 0.5% and at times less than 0.1% w/w at room temperature (20° C.).

The "solid BPO particulate matter" constitutes the "core" of the particles obtained by the process. The solid BPO particulate matter, is, in some embodiments, in such a state of subdivision that it can be suspended in water, e.g. in the form of a finely-divided powder having a $D_{90}$ (see definition below), in some embodiments in the range of 0.3-50 micron. Such a particulate matter can readily be suspended in an aqueous systems by stirring, with or without the aid of a surfactant.

The terms "solid BPO particulate matter" and "particulate matter" will be used interchangeably.

In the present invention the terms "layer", "coating" or "shell" and similar terms, refer to a layer of metal oxide or semi-metal oxide formed around a particle or particulate matter. The layer or coating may not always be complete or uniform and may not necessarily lead to complete coverage of the particulate matter or particle surface. It is appreciated that upon repetition of the coating steps as the coating process proceeds a more uniform coating and more complete coverage of the particulate matter is obtained.

The term "dispersion" as used herein in step (a) of the process refers to a solid dispersion of the particulate matter in the aqueous medium.

Step (a) of the process may further comprise reducing the particle size of the particulate matter to the desired particle size for example by milling or homogenization.

The core (i.e. solid, BPO particulate matter) may be of any shape for example rod-like, plate-like, ellipsoidal, cubic, or spherical shape.

Referring to size of particles will be through their $D_{90}$ meaning that 90% of the particles have the stated dimension or less (measured by volume). Thus, for examples, for spherical particles stated to have a diameter of 10 micrometer ("microns"), this means that the particles have a $D_{90}$ of 10 microns. The $D_{90}$ may be measured by laser diffraction. For particles having a shape other than spheres, the $D_{90}$ refers to the mean average of the diameter of a plurality of particles.

In the case of cores having a spherical shape, the diameter ($D_{90}$) may be in the range of 0.3 to 90 microns, in some embodiments 0.3 to 50 microns, in some other embodiments 1 to 50, in some further embodiments 5 to 30 microns.

By the term "$D_{90}$ may be in the range of 0.3 to 90 microns" is meant that 90% by volume of the particles (in this case the particle's core) may be less than or equal to a value in the range of 0.3 to 90 microns.

For generally cubic-shaped cores or cores having a shape resembling that of a cube, the mean size of a side may be in the range 0.3 to 80 microns, in some embodiments 0.3 to 40 microns, in some further embodiments 0.8 to 40, in some further embodiments 4 to 15 microns.

For rod-like shaped, ellipsoidal-shaped and plate-like shaped cores, the largest dimension (that of the longest axis) is typically in the range 10 to 100 microns, in some embodiments 15 to 50 microns; and the smallest dimension is typically in the range 0.5 to 20 microns, in some further embodiments 2 to 10 microns.

As used herein, unless otherwise indicated, the term "particle" refers to the metal oxide or semi-metal oxide coated particulate matter.

It is appreciated that some of the particles obtained by the process may at times be formed from two or more original particles of the solid BPO particulate and may accordingly include at times more than one core, such cores being separated from each other by a metal oxide region.

The weight of the solid BPO particulate (core material) based on the total weight of the particle may be in the range 99%-50% w/w, in some embodiments in the range 97%-50% w/w. The core material may be in a crystalline form, amorphous form, or combination thereof. The core material may be a cosmetically, pharmaceutically or an agrochemical active ingredient.

In some embodiments, step (c) of the process described above is repeated 4 to about 1000 times. This means that in some embodiments step (b) of the process described above is repeated 4 to about 1000 times.

In further embodiments, the process comprising repeating step (c) 4 to about 300 times, and in some further embodiments 4 to about 100 times. In some other embodiments step (c) of the process described above is repeated 5-80 times in some embodiments 5-50 times. This means that in some embodiments step (b) is repeated as indicated above with respect to step (c).

By the term "repeated 4 to about 1000 times" is meant that the process may be repeated 4, 5, 6, 7, 8, 9 . . . , etc. times up to and including about 1000 times.

According to some embodiments of the present invention step (d) further comprising after aging, separating the coated particulate matter from the dispersing aqueous medium, such as by filtration, centrifugation or decantation and optionally rinsing and re-dispersing the obtained coated particulate matter in an aqueous medium.

In some embodiments, during the coating process at least 50% of the content the particulate matter (pharmaceutical active agent) in the aqueous medium is in a solid state during the coating process.

According to some embodiments of the present invention the process comprising:

(a) contacting the solid, BPO particulate matter, with a first cationic additive and an aqueous medium to obtain a dispersion of said particulate matter having positive charges on its surface;

(b) subjecting the particulate matter to a coating procedure comprising precipitating a metal oxide salt onto the surface of the particulate matter to form a metal oxide coating layer on the particulate matter;

(b1) in an aqueous medium, contacting the coated particulate matter with a surface adhering additive being one or both of (i) a second cationic additive, and (ii) a non-ionic additive;

(b2) subjecting the particulate matter obtained in step (b1) to a coating procedure as in step (b);

(c) repeating steps (b1) and (b2) at least 3 more times; and (d) aging the metal oxide coating layer.

In some embodiments, the process comprising repeating step (c) 3 to about 1000 times.

In some other embodiments, the process comprising repeating step (c) 3 to about 300 times, and in yet further embodiments 3 to about 100 times.

As used herein by the term "repeating step (c) 3 to about 1000 times" is meant that the process may be repeated 3, 4, 5, 6, 7, 8, 9, . . . etc. times up to and including about 1000 times.

This means that in some embodiments steps (b1) and (b2) are repeated as indicted above with respect to step (c).

Additionally according to some embodiments of the present invention the process comprising:

(a) contacting the solid, BPO particulate matter, with an anionic additive, a first cationic additive and an aqueous medium to obtain a dispersion of said particulate matter having positive charges on its surface;

(b) subjecting the particulate matter to a coating procedure comprising precipitating a metal oxide salt onto the surface of the particulate matter to form a metal oxide coating layer on the particulate matter;

(b1) in an aqueous medium, contacting the coated particulate matter with a surface adhering additive being one or both of (i) a second cationic additive, and (ii) a non-ionic additive;

(b2) subjecting the particulate matter obtained in step (b1) to a coating procedure as in step (b);

(c) repeating steps (b1) and (b2) at least 3 more times; and (d) aging the metal oxide coating layer.

When an anionic additive and first cationic additive are used in step (a) of the process, in some embodiments the anionic additive is added before the first cationic additive.

Step (c) may be repeated 3 to about 1000 times. In some embodiments, step (c) is repeated 3 to about 300 times, in some other embodiments, 3 to about 100 times. This means that in some embodiments steps (b1) and (b2) are repeated as indicted above with respect to step (c).

The ionic additive (such as first cationic additive) used in step (a) of the process have a dual effect: to form positive charges on the surface of the particulate matter as will be described below, and also to serve as a wetting agent, thus allowing dispersion of the particulate matter as discrete core particles, where each core particle is individually suspended in the aqueous medium.

Step (a) of the process may be conducted for example by (i) contacting the particulate matter with dry ionic additives and then suspending both in an aqueous medium to obtain a dispersion of said particulate matter having positive charges on its surface, or alternatively by (ii) suspending the solid BPO particulate in an aqueous medium comprising ionic additives to obtain a dispersion of said particulate matter having positive charges on its surface.

According to another embodiment the process may comprise (a) contacting the solid, BPO particulate matter, with an ionic additive selected from (i) an anionic additive; (ii) a first cationic additive, and a combination thereof, and an aqueous medium to obtain a dispersion of said particulate matter having positive charges on its surface; (b), (b1), (b2), (c), (d) are as described herein.

The concentration of the ionic additives in the dispersion can be about 0.001% to about 30%, in some embodiments about 0.01% to about 10% w/w and in some other embodiments about 0.1% up to about 5% w/w.

The solid content of the water dispersion can be about 0.1% to about 80% w/w, in some embodiments about 1% to about 60% w/w, in some further embodiments about 3% to about 50% w/w.

The purpose of step (a) is to modify the electrical charge of the particulate matter by using ionic additives such that it will be made reactive to the attachment of the metal oxide layer.

For preparing the core material of the particles, the particulate matter ought to be suitably coated with an ionic additive (e.g. cationic additive), such that it can be attached to the precipitated metal oxide salt.

In some embodiments, the ionic additive is selected from a cationic additive, an anionic additive, and a combination thereof. The cationic additive may be a cationic surfactant and/or cationic polymer. The anionic additive may be an anionic surfactant and/or anionic polymer.

The particulate matter is contacted with an ionic additive, for example by mixing it with a solution of a cationic surfactant and/or cationic polymer or an anionic surfactant and a cationic additive (e.g. cationic surfactant and/or cationic polymer). Cationic and anionic surfactants are particularly effective in being adsorbed upon the surface of the particulate matter. The ionic additive may also be anionic polymers used in combination with a cationic additive. The cationic surfactant and/or the cationic polymer and optionally further the anionic surfactant (or anionic polymer) need to be used in sufficient amount to provide positive charges on the surface of the particulate matter. The coating need not be continues. It is sufficient that there are at least spots of cationic additive. These spots will then serve as anchors for the attachment of the metal oxide layer. In some embodiments, there are uniform distribution of these anchoring points on the core surface so that as the metal oxide layer builds up it will bridge over and be firmly attached to the core.

According to some embodiments said first and said second cationic additive are the same.

According to another embodiment said first and said second cationic additive are different.

In some other embodiments, the first ionic additive is an anionic surfactant and the second ionic additive is a cationic polymer. In some further embodiments the first cationic additive is a cationic surfactant and the second cationic additive is a cationic polymer.

According to further embodiments, the first cationic additive is a cationic surfactant and the additive in step (b1) is a non-ionic additive (e.g. a non-ionic polymer).

In some further embodiments, the coated particulate matter and the second cationic additive are mixed, and most preferable said mixing is under vigorous stirring (e.g. mixer speed above 1000 rpm).

According to a preferred embodiment of the present invention the process further comprising following step (d): (e) separating the coated particulate matter from the aqueous medium and optionally rinsing and re-dispersing the coated particulate matter in an aqueous medium.

In some embodiments, the separation of the coated particulate matter is conducted by a method such as filtration, centrifugation, decantation, dialysis, or by evaporation of the aqueous medium.

Additionally according to a preferred embodiment of the present invention, step (b) comprises adding a metal oxide salt to the aqueous medium; and optionally acidifying the aqueous medium.

Further according to some embodiments of the present invention, step (b2) comprises adding a metal oxide salt to the aqueous medium; and optionally acidifying the aqueous medium.

In some embodiments step (b1) further comprising adjusting the pH of the dispersion obtained in (b) to a value higher than the isoelectric point of the metal oxide before adding the second cationic additive, in some further embodiments to a pH value of at least about 1 unit higher than the isoelectric point of the metal oxide, before adding the second cationic additive.

In some embodiments, step (b1) further comprising adjusting the pH of the dispersion obtained in (b) to a value higher than the isoelectric point of the metal oxide before adding one or both of (i) a second cationic additive, and (ii) a non-ionic additive, in some embodiments to a pH value of at least about 1 unit higher than the isoelectric point of the metal oxide, before adding one or both of (i) a second cationic additive, and (ii) a non-ionic additive.

For example, in case the metal oxide is silica (e.g. having an isoelectric point in the range 1.7-2.5) the preferred pH may be at least in the range of about 2.5-6.5.

The purpose of the pH adjustment of the dispersion to a value higher than the isoelectric point of the metal oxide is to form negatively charged metal oxide on the particulate matter surface that will be bound to the positive charges of the second cationic additive thus enabling the attachment of the second cationic additive to the surface of the particulate matter.

The non-ionic additive is of a kind that adheres to the surface ("surface-adherent"). An example is a non-ionic polymer. The non-ionic additive may be used alone or in addition to the second cationic surfactant. Without wishing to be bound by theory, the surface-adherent property may be through hydrogen-binding groups such as hydroxyl or amine groups. This allows adhesion of a further layer of metal oxide on the preceding precipitated metal oxide layer.

In some embodiments, the particulate matter/metal oxide salt weight ratio, in each of the steps (b) or (b2) is about 5,000/1 to about 20/1, in some embodiments about 5,000/1 to about 30/1, or about 5,000/1 to about 40/1, in some further embodiments about 1,000/1 to about 40/1, and in yet some further embodiments about 500/1 to about 80/1.

In some embodiments, the particulate matter/cationic additive ratio, in step (b1) is about 25,000/1 to about 50/1, preferably about 5,000/1 to about 100/1, and most preferably about 2000/1 to about 200/1.

According to some embodiments the particulate matter/metal oxide salt weight ratio, in each of the steps (b) or (b2) is about 5,000/1 to about 65/1, and in some further embodiments about 1000/1 to about 100/1.

In some embodiments, the particulate matter/cationic additive weight ratio, in step (b1) is about 10,000/1 to about 100/1, and in some further embodiments about 5000/1 to about 200/1.

The aging in step (d) is crucial for obtaining a strengthened and dense layer of metal oxide.

In some embodiments step (d) comprises raising the pH to a value in the range 3-9 and mixing the suspension in this pH.

According to a preferred embodiment of the present invention step (d) comprises raising the pH to a value in the range 3-9 and mixing the suspension in this pH for a period of at least 2 h.

According to some embodiments of the present invention step (d) comprises raising the pH to a value in the range 3-9, in some further embodiments to a range of 5-7, and mixing, e.g. by stirring, the suspension (dispersion) in this pH range e.g. for a period of at least 2 h (two hours). In some embodiments, stirring is for 2-96 h, in some embodiments 2-72 h, in some other embodiments at least 10 h (for example 10-72 h). In some embodiments the stirring is a gentle stirring, in some embodiments in the range 200-500 rpm.

Upon completion of aging, the separation (e.g. filtration, centrifugation or decantation) will be easy to perform (due to the hard metal oxide layer formed) and the obtained cake or concentrated dispersion will be easily re-dispersed in an aqueous medium to form a dispersion of particles.

The purpose of aging in step (d) is to obtain a strengthened and denser layer of metal oxide.

In the absence of the aging step a thinner and softer layer of metal oxide would be obtained since the metal oxide salt upon precipitation forms a gel layer of metal oxide which may disintegrate or erode upon separation and washing or by mechanical stirring.

The aging may be conducted at a temp of 4-90° C., in some embodiments at 15-60° C. and in further embodiments the aging is conducted at a temperature 20° C.-40° C.

Thus the repeated steps of coating and aging at the end of the process also enable the growth of thicker and stronger layer of metal oxide. In some embodiments aging is not conducted between the repeated coating steps (i.e. between the repeated coating step (b)), but only at the end of the process. Thus in some embodiments the aging is conducted only at the end of the process described herein.

According to certain embodiments, the process may further comprise adding a colloidal metal oxide suspension, in some embodiments aqueous-based suspension (comprising nanometric metal oxide (nanoparticles of metal oxide) during the coating procedure. In some embodiments the colloidal metal oxide suspension is selected from colloidal silica suspension, colloidal titania suspension, colloidal alumina suspension, colloidal zirconia suspension, colloidal ZnO suspension, and mixtures thereof. The colloidal metal oxide suspension may be added during the coating process (e.g. in step (b) in one or more of its repeated steps). In some other embodiments the size of the nanometric metal oxide in diameter is in the range between 5-100 nm (average particle size diameter). The weight ratio of the nanometric metal oxide to the metal oxide salt may be in the range 95:5 to 1:99 in some embodiments 80:20 to 5:95 in some other embodiments 70:30 to 10:90, in yet other embodiments about 60:40 to 20:80. The weight ratio of the nanometric metal oxide to the metal oxide salt may be about 50:50.

According to other embodiments, the process does not include addition of colloidal metal oxide suspension during the coating process. According to this embodiment nanometric metal oxide particles (nanoparticles of metal oxide) are not added during the coating process.

As used herein, the term "metal oxide coating layer" or "metal oxide layer" encompasses the product of both a single processing step as well as a product of the process in which the initially coated particles are further processed, by the repeated processing steps of step (c), described above.

BRIEF DESCRIPTION OF THE DRAWINGS

In order to understand the disclosure and to see how it may be carried out in practice, embodiments will now be described, by way of non-limiting example only, with reference to the accompanying drawings, in which.

DETAILED DESCRIPTION OF EMBODIMENTS

Example 1: Encapsulation of BPO

Figure 1:
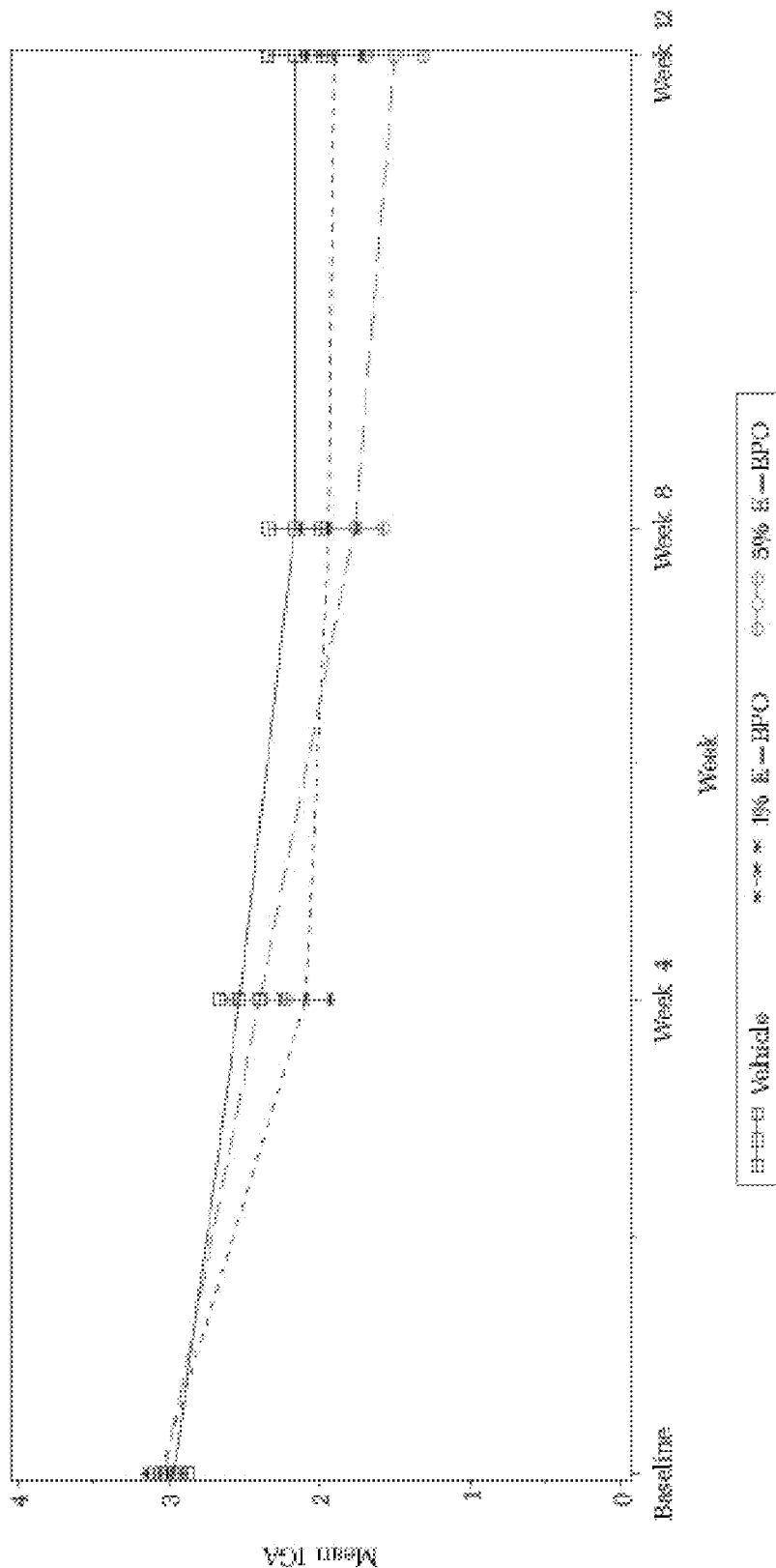
FIG. 1 is a graph presenting the mean IGA per time of BPO composition of the invention (1% and 5% encapsulated BPO as described in example 1) as compared with vehicle alone over a period of time of 12 weeks.

Step 1: milling: 110 g. of hydrous BPO 75% (USP grade from Sigma) were suspended in 152 g. of 0.4% CTAC solution containing 0.001% silicon antifoam. The BPO was milled using a stator rotor mixer (Kinematika polytron 6100 operated at 15,000 rpm/25 m/s). The milling was stopped when the particle size distribution (PSD) of the suspension was d(0.9)<35 μm or the temperature has reached 50 C. The final suspension was cooled to room temperature.

Step 2a: coating option #1: During the coating procedure the suspension was stirred with a mechanical dissolver, 80 mm, at 500 RPM at all times. The pH of the milled BPO suspension was corrected to 8 using NaOH 5N solution. A portion of 1 g of 15% sodium silicate solution (15% w/w as $SiO_2$) was added and the suspension was stirred for 5 min. A portion of 1 g of 3% Polyquatemium 7 was added and the suspension was stirred for 5 min. pH was adjusted to 6-7 using 5N HCl solution.

This procedure was repeated for 5-100 times in order to create a series of silica layers around BPO having different thickness.

Step 2b: coating option #2: During the coating procedure the suspension was stirred with a mechanical dissolver, 80 mm, at 500 RPM at all times. The pH of the milled BPO suspension was corrected to 8 using NaOH 5N solution. A portion of 2.5 g of 15% sodium silicate solution (15% w/w as $SiO_2$) was added and the suspension was stirred for 5 min. A portion of 2.5 g of 3% Polyquatemium 7 was added and the suspension was stirred for 5 min. pH was adjusted to 6-7 using 5N HCl solution.

This procedure was repeated for 5-100 times in order to create a series of silica layers around BPO having different thickness.

The aging step: The coated BPO suspension at pH 6.5 was kept for aging at room temperature (25 C+/−2) under gentle agitation for 24 hrs.

Example 2: Preparation of Encapsulated BPO (15% E-BPO Water Suspension)

a) Preparation of Benzoyl Peroxide Dispersion and Acid Cocktail

A benzoyl peroxide (BPO) dispersion was prepared by mixing 125.67 grams of CTAC CT-429 (Cetrimonium Chloride 30%), 3008 grams of hydrous benzoyl peroxide, and 5200 grams water under high shear. The dispersion was homogenized for 60 minutes at 33° C. (no more than 45° C.), and then the pH of the dispersion was adjusted to 7.0 using sodium hydroxide solution (20%).

An acid cocktail was prepared using 493 grams Hydrochloric acid (37%), 98 grams anhydrous Citric Acid, 147 grams Lactic Acid (90%), and 794 grams water.

b) Coating Cycle

The coating cycle was started by adding 38 grams sodium silicate solution extra pure (28%) to the benzoyl peroxide dispersion prepared in step a) under high shear, followed by adding the acid cocktail prepared in step (a) to adjust the pH to be lower than 6.8, and followed by adding 57 grams PDAC (3%) solution to the mixture. The cycle was repeated 50 times while the mixture was stirred under high shear for 17 hours. After the 50 cycles, the pH of the mixture was adjusted to 5.0 using the acid cocktail, and water was added to complete the total weight of the mixture to 15 kilograms. The composition of the final BPO water suspension product is shown in Table 1.

TABLE 1

Composition of the encapsulated BPO 15% water suspension

| Ingredient | % of ingredient in the suspension |
| --- | --- |
| Polyquarternium-7 | 0.53 |
| Hydrochloric Acid | 0.87 |
| Citric Acid, Anhydrous | 0.46 |
| Lactic Acid | 0.63 |
| Silicon Dioxide | 3.42 |
| Sodium hydroxide | 0.01 |
| Cetrimonium Chloride | 0.25 |
| Hydrous Benzoyl Peroxide | 15.00 |
| Sterile Water for Irrigation | Up to 100% |

Example 3: Preparation of Formulation of Encapsulated BPO (5%) Gel (Formulation I)

Oil Phase: 720.0 of grams Cyclomethicone 5-N, 540.0 of grams Cetyl Alcohol, 360.0 grams Polyoxyl 100 Stearate, and 540.0 grams of Glyceryl Monosterate were mixed at 70° C.

Water phase: 18.0 grams of Ethylendiaminetetraacetate Disodium salt were dissolved in 6500 grams of water. 720.0 grams of glycerin (99.5%) were added to the solution. After the solution was heated to 70° C., 72.0 grams of Carbopol 980 NF were added and the resulting mixture was homogenized at 3300 rpm for 10 minutes to ensure that all materials completely melted and dissolved. 76.5 grams if sodium hydroxide (20%) were then added and the mixture was stirred under high shear for 10 minutes at no less than 70° C.

The oil phase was added to the water phase under high shear at 78° C., and the resulting emulsion was homogenized at 3300 rpm for 10 minutes. 72.0 grams of Citric Acid and 6,000 grams of encapsulated BPO 15% water suspension made as described in Example 2 were mixed. The resulting mixture was added to the emulsion at 65° C. and mixed at 1400 rpm for 10 minutes. The emulsion was cooled to 35° C. and the pH of the emulsion was adjusted to 4.0 using HCl 5N solution. The emulsion was stirred at 1400 rpm for 10 minutes and then water was added until the total weight of the emulsion reached 18 kilograms. The composition of the formulation prepared in this example is shown in Table 2.

TABLE 2

Composition of Formulation I

| Ingredient | % of pure ingredient in the composition |
| --- | --- |
| Polyquarternium-7 | 0.17 |
| Hydrochloric Acid | 0.37 |
| Citric Acid, Anhydrous | 0.38 |
| Lactic Acid | 0.21 |
| Silicon Dioxide | 1.14 |
| Sodium hydroxide | 0.08 |
| Cetrimonium Chloride | 0.1 |
| Hydrous Benzoyl Peroxide | 5.00 |
| Glycerin | 4.00 |
| Polyoxyl 100 stearate | 2.00 |

TABLE 2-continued

Composition of Formulation I

| Ingredient | % of pure ingredient in the composition |
|---|---|
| Cetyl alcohol | 3.00 |
| Cyclomethicone | 4.00 |
| Glyceryl monostearate | 3.00 |
| Edetate Disodium | 0.10 |
| Carbopol 980 | 0.40 |
| Sterile Water for Irrigation | up to 100% |

Example 4: Preparation of Placebo of Encapsulated BPO Water Suspension a) Preparation of Placebo Dispersion and Acid Cocktail A placebo dispersion was prepared by mixing 125.67 grams of CTAC CT-429 (Cetrimonium Chloride 30%), and 5200 grams and then the pH of the solution was adjusted to 7.0 using sodium hydroxide solution (20%).

An acid cocktail was prepared using 493 grams Hydrochloric acid (37%), 98 grams anhydrous Citric Acid, 147 grams Lactic Acid (90%), and 794 grams water.

b) Coating Cycle

The coating cycle was started by adding 38 grams sodium silicate solution extra pure (28%) to the placebo solution prepared in step a) under high shear, followed by adding the acid cocktail prepared in step (a) to adjust the pH to be lower than 6.8, and followed by adding 57 grams PDAC (3%) solution to the mixture. The cycle was repeated 50 times while the mixture was stirred under high shear for 17 hours. After the 50 cycles, the pH of the mixture was adjusted to 5.0 using the acid cocktail, and water was added to complete the total weight of the mixture to 15 kilograms. The composition of the final placebo water suspension product is shown in Table 3.

TABLE 3

Composition of placebo of encapsulated BPO water suspension

| Ingredient | % of ingredient in the suspension |
|---|---|
| Polyquarternium-7 | 0.53 |
| Hydrochloric Acid | 0.87 |
| Citric Acid, Anhydrous | 0.46 |
| Lactic Acid | 0.63 |
| Silicon Dioxide | 3.42 |
| Sodium hydroxide | 0.01 |
| Cetrimonium Chloride | 0.25 |
| Sterile Water for Irrigation | Up to 100% |

Example 5: Preparation of Formulation of Vehicle of Encapsulated BPO Gel (Formulation II)

Oil Phase: 720.0 of grams Cyclomethicone 5-N, 540.0 of grams Cetyl Alcohol, 360.0 grams Polyoxyl 100 Stearate, and 540.0 grams of Glyceryl Monosterate were mixed at 70° C.

Water phase: 18.0 grams of Ethylendiaminetetraacetate Disodium salt were dissolved in 6500 grams of water. 720.0 grams of glycerin (99.5%) were added to the solution. After the solution was heated to 70° C., 72.0 grams of Carbopol 980 NF were added and the resulting mixture was homogenized at 3300 rpm for 10 minutes to ensure that all materials completely melted and dissolved. 76.5 grams if sodium hydroxide (20%) were then added and the mixture was stirred under high shear for 10 minutes at no less than 70° C.

The oil phase was added to the water phase under high shear at 78° C., and the resulting emulsion was homogenized at 3300 rpm for 10 minutes. 72.0 grams of Citric Acid and 6,000 grams of placebo of encapsulated BPO water suspension made as described in Example 4 were mixed. The resulting mixture was added to the emulsion at 65° C. and mixed at 1400 rpm for 10 minutes. The emulsion was cooled to 35° C. and the pH of the emulsion was adjusted to 4.0 using HCl 5N solution. The emulsion was stirred at 1400 rpm for 10 minutes and then water was added until the total weight of the emulsion reached 18 kilograms. The composition of the formulation prepared in this example is shown in Table 4.

TABLE 4

Composition of Formulation II

| Ingredient | % of pure ingredient in the composition |
|---|---|
| Polyquarternium-7 | 0.17 |
| Hydrochloric Acid | 0.37 |
| Citric Acid, Anhydrous | 0.38 |
| Lactic Acid | 0.21 |
| Silicon Dioxide | 1.14 |
| Sodium hydroxide | 0.08 |
| Cetrimonium Chloride | 0.1 |
| Glycerin | 4.00 |
| Polyoxyl 100 stearate | 2.00 |
| Cetyl alcohol | 3.00 |
| Cyclomethicone | 4.00 |
| Glyceryl monostearate | 3.00 |
| Edetate Disodium | 0.10 |
| Carbopol 980 | 0.40 |
| Sterile Water for Irrigation | up to 100% |

Example 6: Preparation of Formulation of Encapsulated BPO (1%) Gel (Formulation III)

Oil Phase: 720.0 of grams Cyclomethicone 5-N, 540.0 of grams Cetyl Alcohol, 360.0 grams Polyoxyl 100 Stearate, and 540.0 grams of Glyceryl Monosterate were mixed at 70° C.

Water phase: 18.0 grams of Ethylendiaminetetraacetate Disodium salt were dissolved in 6500 grams of water. 720.0 grams of glycerin (99.5%) were added to the solution. After the solution was heated to 70° C., 72.0 grams of Carbopol 980 NF were added and the resulting mixture was homogenized at 3300 rpm for 10 minutes to ensure that all materials completely melted and dissolved. 76.5 grams if sodium hydroxide (20%) were then added and the mixture was stirred under high shear for 10 minutes at no less than 70° C.

The oil phase was added to the water phase under high shear at 78° C., and the resulting emulsion was homogenized at 3300 rpm for 10 minutes. 72.0 grams of Citric Acid, 1200 grams of encapsulated BPO 15% water suspension made as described in Example 2 and 4800 grams of placebo of encapsulated BPO water suspension as described in Example 4 were mixed. The resulting mixture was added to the emulsion at 65° C. and mixed at 1400 rpm for 10 minutes. The emulsion was cooled to 35° C. and the pH of the emulsion was adjusted to 4.0 using HCl 5N solution. The emulsion was stirred at 1400 rpm for 10 minutes and then water was added until the total weight of the emulsion reached 18 kilograms. The composition of the formulation prepared in this example is shown in Table 5.

TABLE 5

Composition of Formulation III

| Ingredient | % of pure ingredient in the composition |
| --- | --- |
| Polyquarternium-7 | 0.17 |
| Hydrochloric Acid | 0.37 |
| Citric Acid, Anhydrous | 0.38 |
| Lactic Acid | 0.21 |
| Silicon Dioxide | 1.14 |
| Sodium hydroxide | 0.08 |
| Cetrimonium Chloride | 0.1 |
| Hydrous Benzoyl Peroxide | 1.00 |
| Glycerin | 4.00 |
| Polyoxyl 100 stearate | 2.00 |
| Cetyl alcohol | 3.00 |
| Cyclomethicone | 4.00 |
| Glyceryl monostearate | 3.00 |
| Edetate Disodium | 0.10 |
| Carbopol 980 | 0.40 |
| Sterile Water for Irrigation | up to 100% |

Example 7: Efficacy Study of BPO in a Composition of the Invention

A multi-center, double-blind, randomized, vehicle-controlled, dose-range study was performed. Study duration was 12 weeks on mild to severe facial rosacea patients using encapsulated benzoyl peroxide gel, 1% (as described in Example 6) and 5% (as described in Example 3), and vehicle gel (as described in Example 5) once daily.

A total of 92 subjects were randomly assigned in a 1:1:1 ratio to 5% E-BPO Gel, 1% E BPO Gel, or Vehicle Gel.

The investigator performed the Investigator Global Assessment (IGA) and inflammatory lesion (papules and pustules) counts at Screening, Baseline, and Weeks 4, 8, and 12 (end of study).

Evaluation of Efficacy:

The first application of the test product was applied at the investigational site at the end of the Baseline visit (Day 0) under the supervision and instruction of the designated investigational site staff. The investigator performed the Investigator Global Assessment (IGA) and inflammatory lesion (papules and pustules) counts at Screening, Baseline, and Weeks 4, 8, and 12 (end of study) and erythema and telangiectasia assessments at Baseline, and Weeks 4, 8, and 12 (end of study). The evaluator also assessed local application site irritation (dryness, scaling, pruritus, stinging and burning) at Baseline and Weeks 2, 4, 8 and 12 (end of study). At selected investigational site(s), standardized photography of facial rosacea also was performed at Baseline and Week 8 and 12 (end of study). Information on adverse events (AEs) was collected at all visits.

Efficacy endpoints were: Proportion of subjects with the primary measure of success, defined as a 2-grade improvement in the IGA relative to Baseline at Week 12, with the Week 12 IGA of clear or almost clear. Change in inflammatory lesion count at Week 12.

Results:

Baseline Characteristics: The Baseline characteristics were similar among the treatment groups for IGA and telangiectasia. While the median inflammatory lesion counts were similar among the treatment groups, the mean inflammatory lesion count was numerically higher for 1% E-BPO Gel than for 5% E-BPO Gel and for 1% E-BPO Gel and 5% E-BPO Gel than for Vehicle Gel, and a numerically higher proportion of subjects in 1% E-BPO Gel than in 5% E-BPO Gel and 1% E-BPO Gel and 5% E-BPO Gel than in Vehicle Gel had severe inflammatory lesion erythema at Baseline. A numerically higher proportion of subjects in 1% E-BPO Gel and 5% E-BPO Gel than in Vehicle Gel had severe rosacea erythema Primary Efficacy Analyses For the Primary Efficacy Endpoints:

The proportions of subjects with the primary measure of success (defined as a 2-grade improvement in the IGA relative to Baseline at Week 12, with the Week 12 IGA of clear or almost clear) were 20.0% (6/30) for Vehicle Gel, 37.5% (12/32) for 1% E-BPO Gel, and 53.3% (16/30) for 5% E-BPO Gel. The improvement in mean IGA is described in FIG. 1.

Figure 2:
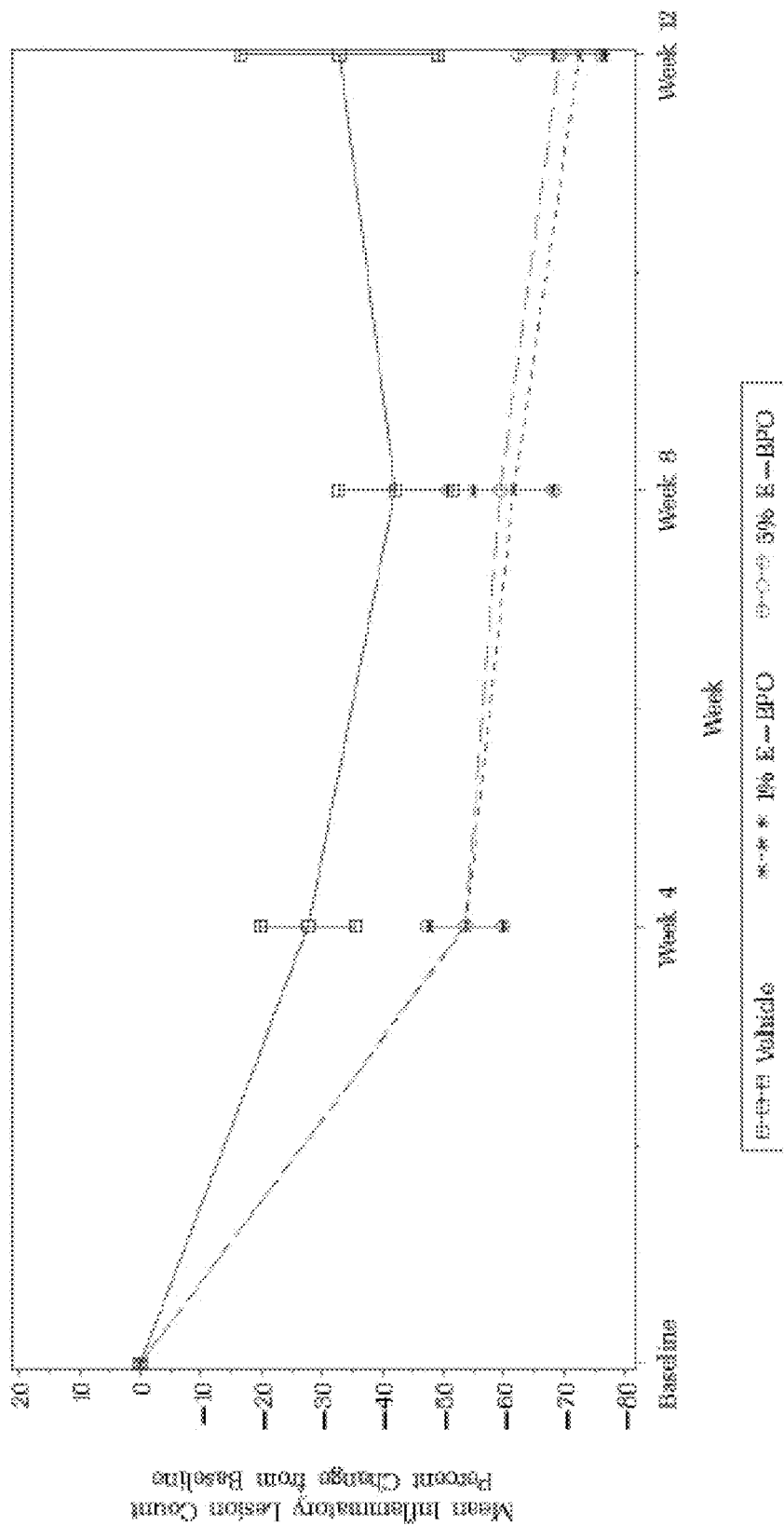
FIG. 2 is a graph presenting the is the mean inflammatory lesion count per time of BPO composition of the invention (1% and 5% encapsulated BPO as described in example 1) as compared with vehicle alone over a period of time of 12 weeks.

The proportions of subjects with the $2^{nd}$ primary measure of success (defined as mean inflammatory lesion count percent change from Baseline at Week 12) were about 30.0% for Vehicle Gel and more than 60% for 1% E-BPO Gel and 5% E-BPO Gel The improvement in inflammatory lesion count is described in FIG. 2.

Example 8: Measuring the Dissolution Rate of BPO from a Composition of the Invention Weighing of Samples A sample was weighed according to its BPO content in amount equivalent to 40 mg of BPO. Examples for weight of samples are given in the table below.

| | Concentration of BPO in the sample ($C_0$) | | |
| --- | --- | --- | --- |
| | 1% (w/w) | 5% (w/w) | 10% (w/w) |
| Weight of sample, mg | 3200-4800 | 640-960 | 320-480 |

Preparation of Samples and Measurement Procedure

The sample was weighed into a 250 mL Erlenmeyer flask, 200 mL of "medium" were added and a 3.0 cm length magnetic bar was inserted, the flask was placed on the stirrer and stirring at 400 rpm was started. 2 mL at specified time intervals were withdrawn and filtered through 0.2 μm GHP Acrodisc syringe filter (first mL discarded). The concentration of BPO (in % w/w) dissolved in each time interval ($C_n$) were calculated.

The "medium" was prepared by mixing 550 mL of water with 450 mL of acetonitrile, which were than equilibrated to ambient temperature.

The dissolution rate was measured according to the following formula:

$$\text{The dissolution rate } (\%) = (C_n/C_0)*100\%$$

Dissolution Rate of BPO in Compositions of the Invention

Figure 3:
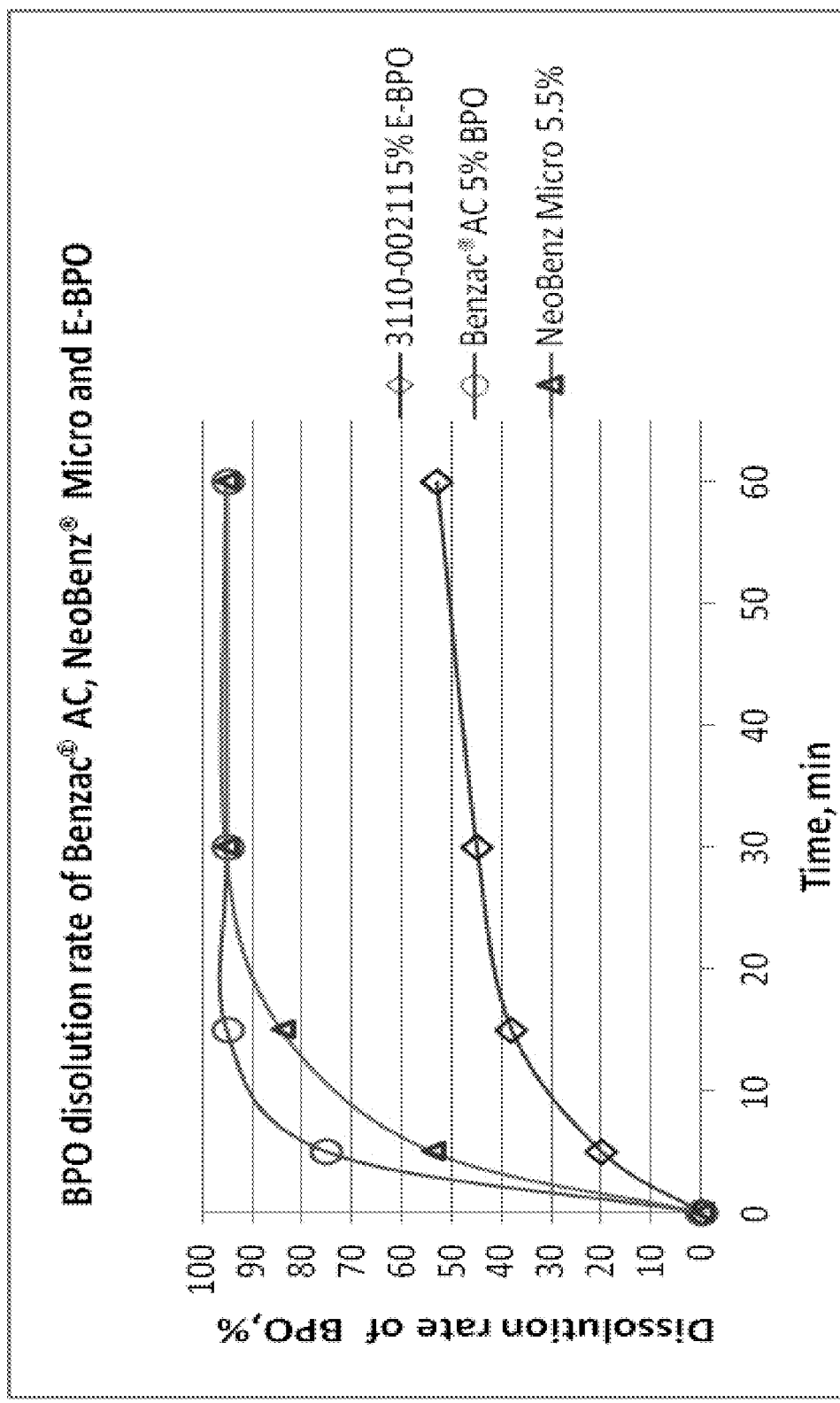
FIG. 3 is a graph presenting the dissolution rate of BPO over a period of 60 minutes of a composition of the invention (5% E-BPO, produced according to Example #3), and Benzac® AC 5% BPO and NeoBenz® Micro 5.5%.

The dissolution rate of a composition of the invention comprising 5% E-BPO, produced according to Example #3, were compared with the dissolution of Benzac® AC 5% BPO and NeoBenz® Micro 5.5%. As can be seen from the results presented in FIG. 3, the dissolution rate of a composition of the invention was much lower than the dissolution of the above commercial products.

The invention claimed is:

1. A composition for the topical treatment of rosacea, comprising:
   a pharmaceutical acceptable topical vehicle, and as the sole pharmaceutical active agent, benzoyl peroxide in solid form,
   wherein said vehicle is an oil-in-water emulsion comprising a polyoxylstearate, a glyceryl stearate, and at least one fatty alcohol, wherein the ratio of said polyoxylstearate to said glyceryl stearate is in the range of 0.1:10 to 10:0.1,
   wherein said solid benzoyl peroxide is encapsulated as the core of a microcapsule having a shell comprising at least one inorganic polymer, said core consisting of said solid benzoyl peroxide, and
   wherein said composition has a dissolution rate of less than 60% weight/h as measured in a medium of a mixture of water and acetonitrile at ambient temperature.

2. A composition according to claim 1, wherein said benzoyl peroxide is at least 1.0% by weight of said composition.

3. A composition according to claim 1, wherein said benzoyl peroxide is present in the composition in an amount of about 2.5% to about 10% by weight of said composition.

4. A composition according to claim 1, wherein said benzoyl peroxide is in a crystalline form.

5. A composition according to according to claim 1, further comprising at least one additive, which additive is not a pharmaceutical active agent, selected from the group consisting of at least one of chelating agents, antioxidants, sunscreens, preservatives, fillers, electrolytes, humectants, dyes, mineral or organic acids or bases, fragrances, essential oils, moisturizers, vitamins, essential fatty acids, sphingolipids, self-tanning compounds, calmatives and skin-protecting agents, and pro-penetrating agents and gelling agents.

6. The composition of claim 1, wherein said composition further comprises a polyacrylic acid homopolymer or copolymer.

7. The composition of claim 1, wherein said oil in said oil in water emulsion is selected from the group consisting of paraffin oil, isopropyl myristate, caprylic/capric triglyceride, squalane, squalene, almond oil, castor oil, olive oil, jojoba oil, sunflower oil, soybean oil, grape seed oil, dimethicone, cyclomethicone and mixtures thereof.

8. A composition according to claim 1, wherein said composition is in a gel form comprising at least one non-ionic polymeric dispersant and at least one thickening agent.

9. The composition of claim 8, wherein said at least one non-ionic polymeric dispersant is selected from the group consisting of poly vinyl pyrrolidone (PVP), poly vinyl pyrrolidone-co-vinyl acetate, polyamide, polyurethane, polyurea and mixtures thereof.

10. The composition of claim 8, wherein said at least one thickening agent is selected from the group consisting of at least one of hydroxy propyl cellulose (HPC), hydroxyl ethyl cellulose (HEC), hydroxyl methyl cellulose (HMC), polyacrylic acid homopolymer, polyacrylic acid copolymer, fatty alcohol, silica and its derivatives, xanthan gum, arabic gum, poly vinyl alcohol, veegum, laponite, and clay.

11. The composition of claim 8, wherein said composition further comprises glycerin.

12. A method for the topical treatment of rosacea, comprising, topically administering to a patient in need, an effective amount of the composition in accordance with claim 1.

* * * * *